US010506939B2

(12) United States Patent
Rubinstein et al.

(10) Patent No.: US 10,506,939 B2
(45) Date of Patent: Dec. 17, 2019

(54) MATCHING AND TRACKING TIME SEQUENCES OF HEART ACTIVATION

(71) Applicant: BIOSENSE WEBSTER (ISRAEL) LTD., Yokneam (IL)

(72) Inventors: Vladimir Rubinstein, Haifa (IL); Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 365 days.

(21) Appl. No.: 15/206,418

(22) Filed: Jul. 11, 2016

(65) Prior Publication Data

US 2017/0042443 A1    Feb. 16, 2017

Related U.S. Application Data

(60) Provisional application No. 62/203,422, filed on Aug. 11, 2015.

(51) Int. Cl.
*A61B 5/0452* (2006.01)
*A61B 5/042* (2006.01)
(Continued)

(52) U.S. Cl.
CPC .......... *A61B 5/04525* (2013.01); *A61B 5/044* (2013.01); *A61B 5/04012* (2013.01); *A61B 5/0422* (2013.01)

(58) Field of Classification Search
CPC .................................................. A61B 5/6852
See application file for complete search history.

(56) References Cited

U.S. PATENT DOCUMENTS

| 5,545,186 A | 8/1996 | Olson et al. |
| 6,477,406 B1 | 11/2002 | Turcott |

(Continued)

FOREIGN PATENT DOCUMENTS

| WO | WO 2001/03578 A2 | 1/2001 |
| WO | WO 2014/174274 A1 | 10/2014 |

OTHER PUBLICATIONS

European Search Report dated Jan. 12, 2017 in corresponding European Patent Application No. 16183500.4.

(Continued)

*Primary Examiner* — Carl H Layno
*Assistant Examiner* — Jennifer L Ghand
(74) *Attorney, Agent, or Firm* — Lewis Roca Rothgerber Christie LLP (57) ABSTRACT

A method, including, receiving a first group of electrocardiograph (ECG) signals derived from a single heartbeat and generated at a respective plurality of electrodes on a catheter in a heart of a subject, formulating a template relating times of annotations of the first group of the ECG signals, and assigning the template an index. The method further includes receiving a second group of ECG signals derived from a subsequent single heartbeat and generated at the electrodes, calculating times of annotations of the second group, formulating a comparison between the template and the times of annotations of the second group, and, when the comparison indicates that the times of annotations of the second group correspond to the template, assigning the index to the second group of ECG signals, and presenting graphically on a display an occurrence of the template relative to a timeline representing heartbeats from the heart.

23 Claims, 7 Drawing Sheets

(51) Int. Cl.
   *A61B 5/04*      (2006.01)
   *A61B 5/044*     (2006.01)

(56) References Cited

U.S. PATENT DOCUMENTS

| | | | |
|---|---|---|---|
| 2004/0019366 A1 | 1/2004 | Rottenberg et al. | |
| 2005/0004608 A1* | 1/2005 | Bullinga | A61N 1/3702 607/9 |
| 2005/0137485 A1 | 6/2005 | Cao et al. | |
| 2006/0161069 A1 | 7/2006 | Li | |
| 2009/0112106 A1 | 4/2009 | Zhang | |
| 2012/0184858 A1* | 7/2012 | Harlev | A61B 5/0402 600/484 |
| 2013/0123652 A1* | 5/2013 | Rubinstein | A61B 5/7203 600/509 |
| 2014/0180051 A1 | 6/2014 | Thakur et al. | |
| 2014/0343388 A1 | 11/2014 | Thakur et al. | |
| 2015/0208938 A1 | 7/2015 | Houben et al. | |

OTHER PUBLICATIONS

Pascale, M.D., Patrizio et al., Pattern and Timing of the Coronary Sinus Activation to Guide Rapid Diagnosis of Atrial Fibrillation Ablation, Circulation Arrhythmia Electrophysiology, Jun. 2013, pp. 481-490.

\* cited by examiner

MATCHING AND TRACKING TIME SEQUENCES OF HEART ACTIVATION

CROSS-REFERENCE TO RELATED APPLICATION

This application claims the benefit of U.S. Provisional Patent Application 62/203,422, filed Aug. 11, 2015, which is incorporated herein by reference.

FIELD OF THE INVENTION

This invention relates generally to analysis of electrocardiograph (ECG) signals, and specifically to analysis of groups of such signals.

BACKGROUND OF THE INVENTION

An article titled "Pattern and Timing of the Coronary Sinus Activation to Guide Rapid Diagnosis of Atrial Tachycardia After Atrial Fibrillation Ablation' by Pascale et al, published in Circ Arrhythm Electrophysiol. 2013, is incorporated herein by reference. In the article, the authors state that atrial tachycardias (AT) during or after ablation of atrial fibrillation frequently pose a diagnostic challenge. The authors hypothesize that both the patterns and the timing of coronary sinus (CS) activation could facilitate AT mapping.

U.S. Patent Application 2015/0208938, to Houben et al., whose disclosure is incorporated herein by reference, describes detection of an activation wavefront generated in the heart, using bipolar and unipolar electrograms.

The description above is presented as a general overview of related art in this field and should not be construed as an admission that any of the information it contains constitutes prior art against the present patent application.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:

receiving a first group of electrocardiograph (ECG) signals derived from a single heartbeat and generated at a respective plurality of electrodes on a catheter in a heart of a subject;

formulating a template relating times of annotations of the first group of the ECG signals, and assigning the template an index;

receiving a second group of ECG signals derived from a subsequent single heartbeat and generated at the plurality of electrodes;

calculating times of annotations of the second group of ECG signals;

formulating a comparison between the template and the times of annotations of the second group; and when the comparison indicates that the times of annotations of the second group correspond to the template, assigning the index to the second group of ECG signals, and presenting graphically on a display an occurrence of the template relative to a timeline representing heartbeats from the heart.

A disclosed embodiment includes using the first group and the second group to formulate a common map of the heart.

A further disclosed embodiment includes, when the comparison indicates that the times of annotations of the second group do not correspond to the template, formulating a further template relating the times of annotations of the second group of the ECG signals, and assigning the further template a further index, and presenting graphically on the display a further occurrence of the further template relative to the timeline. Typically, the method includes using the first group to formulate a first map of the heart, and the second group to formulate a second map, different from the first map of the heart.

A yet further disclosed embodiment includes receiving a stream of channel annotations, slicing the stream into segments corresponding to respective heartbeats, estimating a reference annotation as one of an average, a weighted average, or a median, of the channel annotations of the segments in the stream, and applying the reference annotation in formulating the template. Typically, the template includes differences between the times of annotations of the first group with the reference annotation.

In an alternative embodiment the catheter is located in a coronary sinus of the heart.

In a further alternative embodiment the plurality of electrodes are evenly spaced along the catheter.

In a yet further alternative embodiment the catheter is linear.

In some embodiments the template is assigned to a first type of arrhythmia, and the method further includes receiving a subsequent group of ECG signals, and monitoring if the times of annotations of the subsequent group do not correspond to the template, thus indicating that the subsequent group of ECG signals corresponds to a second type of arrhythmia, different from the first type.

There is further provided, according to an embodiment of the present invention, apparatus, including:

a catheter, located in a heart of a subject and configured to:

receive a first group of electrocardiograph (ECG) signals derived from a single heartbeat and generated at a respective plurality of electrodes on the catheter, and receive a second group of ECG signals derived from a subsequent single heartbeat and generated at the plurality of electrodes;

a processor configured to:

formulate a template relating times of annotations of the first group of the ECG signals, and assign the template an index, calculate times of annotations of the second group of ECG signals, formulate a comparison between the template and the times of annotations of the second group, and when the comparison indicates that the times of annotations of the second group correspond to the template, assign the index to the second group of ECG signals; and a display configured to present graphically an occurrence of the template relative to a timeline representing heartbeats from the heart.

The present disclosure will be more fully understood from the following detailed description of the embodiments thereof, taken together with the drawings, in which:

DETAILED DESCRIPTION OF EMBODIMENTS

Overview

The time patterns of the coronary sinus (CS) activations can be helpful in atrial tachycardia (AT) mapping. The analysis of time patterns of CS activation provides a rapid stratification, or ordering, of most likely macro-reentrant ATs, and the analysis also points toward the likely origin of focal ATs.

The inventors have developed a method that analyzes multi-channel unipolar ECG signals so as to match and track time patterns of the signals. In one embodiment, the method finds, and keeps track of, certain "time configuration of activities" specific to different types of cardiac behavior. A "time configuration of activities," also referred to herein as a "time pattern," corresponds to specific time interrelations between unipolar annotations of the ECG signals. The annotations correspond to a local activation time (LAT) of the signal.

LAT maps, derived from the ECG signals, may be used in analyzing functioning of the heart, and such maps are constructed by the CARTO® system, produced by Biosense-Webster of Diamond Bar CA. The maps typically illustrate the results produced by several mechanisms of electrical wave generation in the heart under arrhythmias. Embodiments of the present invention may automatically separate and track these different mechanisms so as to build LAT maps that may contain only a single type of the heart activation. Embodiments of the present invention enable faster and more accurate production of LAT maps.

Detailed Description

1. Introduction

Figure 1:
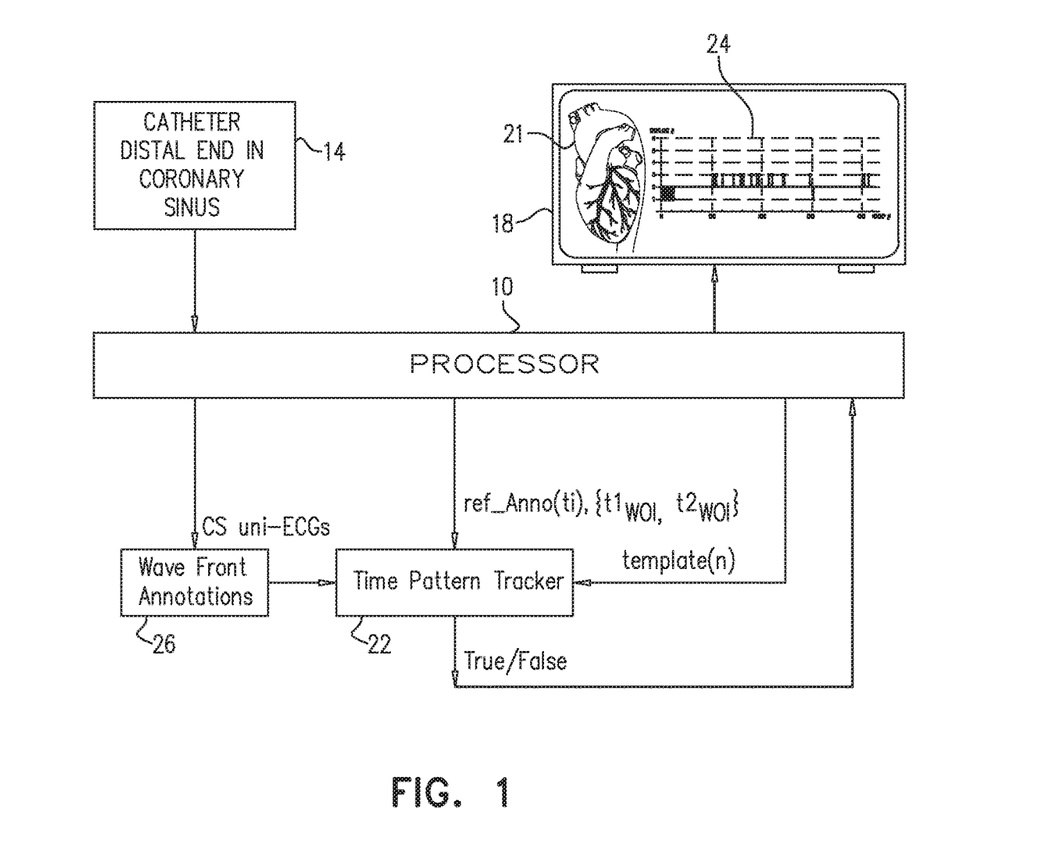
FIG. 1 is a schematic block diagram illustrating operation of a signal analyzing algorithm, according to an embodiment of the present invention.

FIG. 1 is a schematic block diagram illustrating operation of a signal analyzing algorithm, according to an embodiment of the present invention. The algorithm is operated by a processor 10 which receives multiple electrocardiograph (ECG) signals from a reference catheter distal end 14 that is located in the coronary sinus (CS), and results of the operation of the algorithm may be presented by the processor on a display 18 of the system. Results of the operation may be incorporated into a map 21 of the heart, and/or in the form of a graph 24, and both types of results are described below. In one embodiment catheter distal end 14 is approximately linear and has ten (10) electrodes evenly spaced along the distal end. In some embodiments the electrodes are arranged in pairs.

As is described in more detail below, the algorithm analyzes incoming ECG signals of the reference catheter, and from the analysis identifies different types of uniform heart activations. The heart activations are supplied to an LAT mapping procedure, and the algorithm may also be used as a filter that indicates when to acquire a new point in the mapping procedure. Elements used to implement the algorithm, i.e., the processor, the catheter, and the display, may be present in the CARTO® system referenced above. The algorithm may be used in real-time analysis of ECG signals, and/or for analysis of recorded signals.

The processor uses a time pattern tracker block 22, to determine and keep track of "time configuration of activities" or "time patterns" that describe specific time interrelations between annotations, or LATs, of ECG signals. As is illustrated in FIG. 1, the processor sets a time interval, a window of interest, $\{ref\_Anno(t_i)-\tau_1 WOI, ref\_Anno(t_i)+\tau_2 WOI\}$ when the track is to operate. ($t_i$ is an identifying time of the time interval, $\tau_1 WOI$ is an initial time of the interval, and $\tau_2 WOI$ is a final time of the interval.) During this interval the tracker receives results of Wave Front annotation calculations performed by the processor on the ECG signals. The calculations are performed in a wave front annotation block 26, wherein the processor operates a wavefront algorithm to calculate the annotation time for each ECG signal. A suitable algorithm is described in U.S. Patent Application 2015/0208938, referenced above.

The tracker estimates a similarity of the current activation to a pre-set template (Template(n), where n, a positive integer, is a template index. A template is a descriptor of a time pattern of annotations.

As described below, the algorithm run by processor 10 and tracker block 22 may operate in two modes, a template tracking (TT) mode wherein the time pattern is calculated from incoming ECG signals and is compared with an existing (pre-set) template, and a template matching (TM) mode wherein new templates may be generated from the signals.

2. Calculation of a Time Pattern

To calculate the time pattern of a plurality of the CS reference channels the processor annotates each channel of a given heartbeat (in a given time interval comprising the heartbeat)—annUniChn(k, ti), where k is an index of the channels, forming a group of annotations. The processor then calculates a weighted average wAverage(ti) of the group of annotations according to equation (1):

$$wAverage(t_i) = \Sigma_k^K \left| \frac{dUni(k, t_i)}{dt} \right| * annUniChn(k, t_i) / \Sigma_k^K \left| \frac{dUni(k, t_i)}{dt} \right| \quad (1)$$

where Uni(k, ti) is the $k^{th}$ ECG signal in the time interval $\{ref\_Anno(t_i)-\tau_1 WOI, ref\_Anno(t_i)+\tau_2 WOI\}$, annUniChn(k, ti) is the annotation of the $k^{th}$ ECG signal, $$\frac{dUni(k, t_i)}{dt}$$

is a derivative of the $k^{th}$ ECG signal in a neighborhood of the annotation annUniChn(k, ti), and k is the total number of channels, i.e., the total number of electrodes on the CS catheter distal end.

Figure 2:
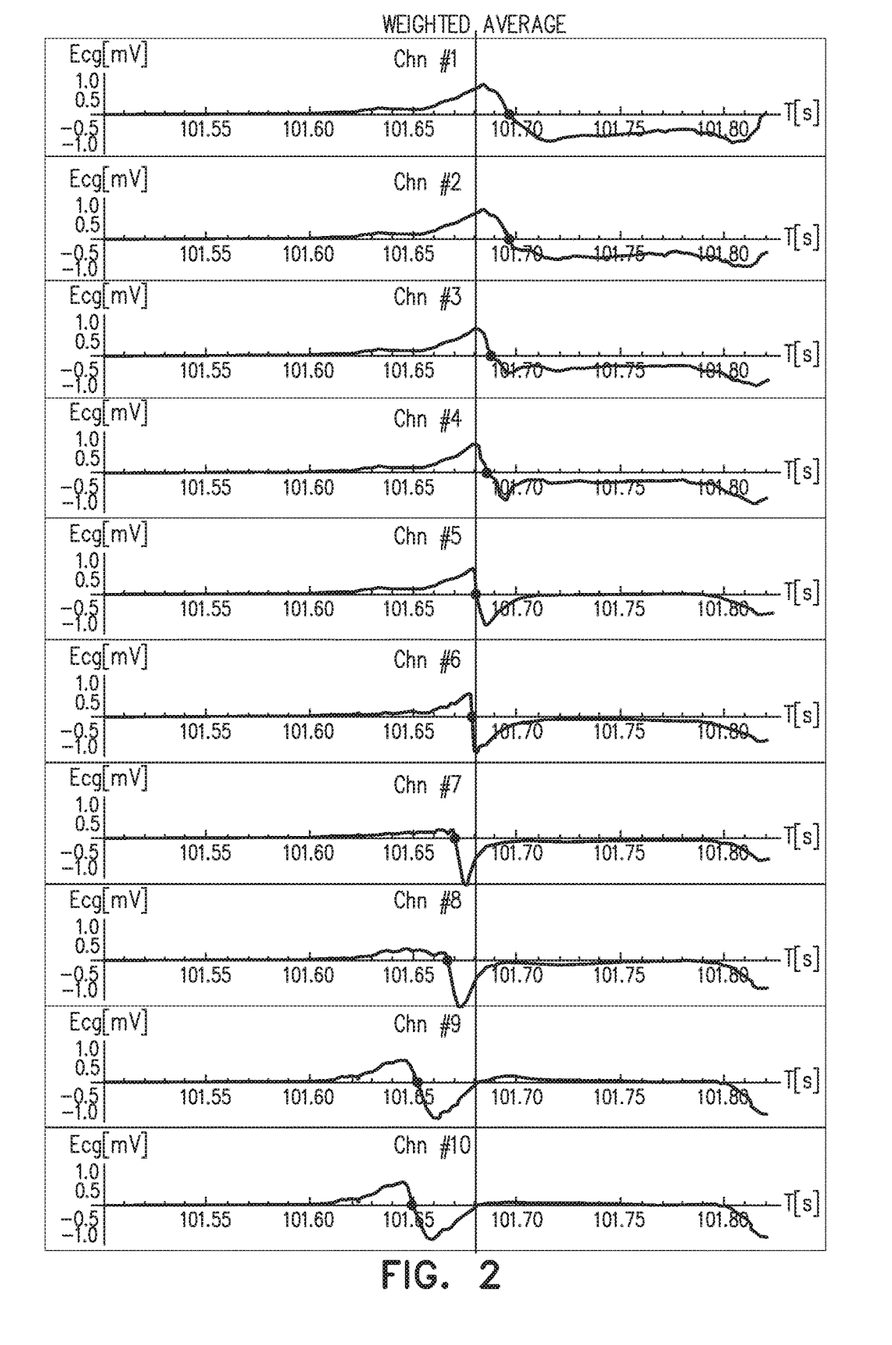
FIG. 2 is an example of unipolar ECG signals with their annotations and their weighted average, according to an embodiment of the present invention.
Figure 3:
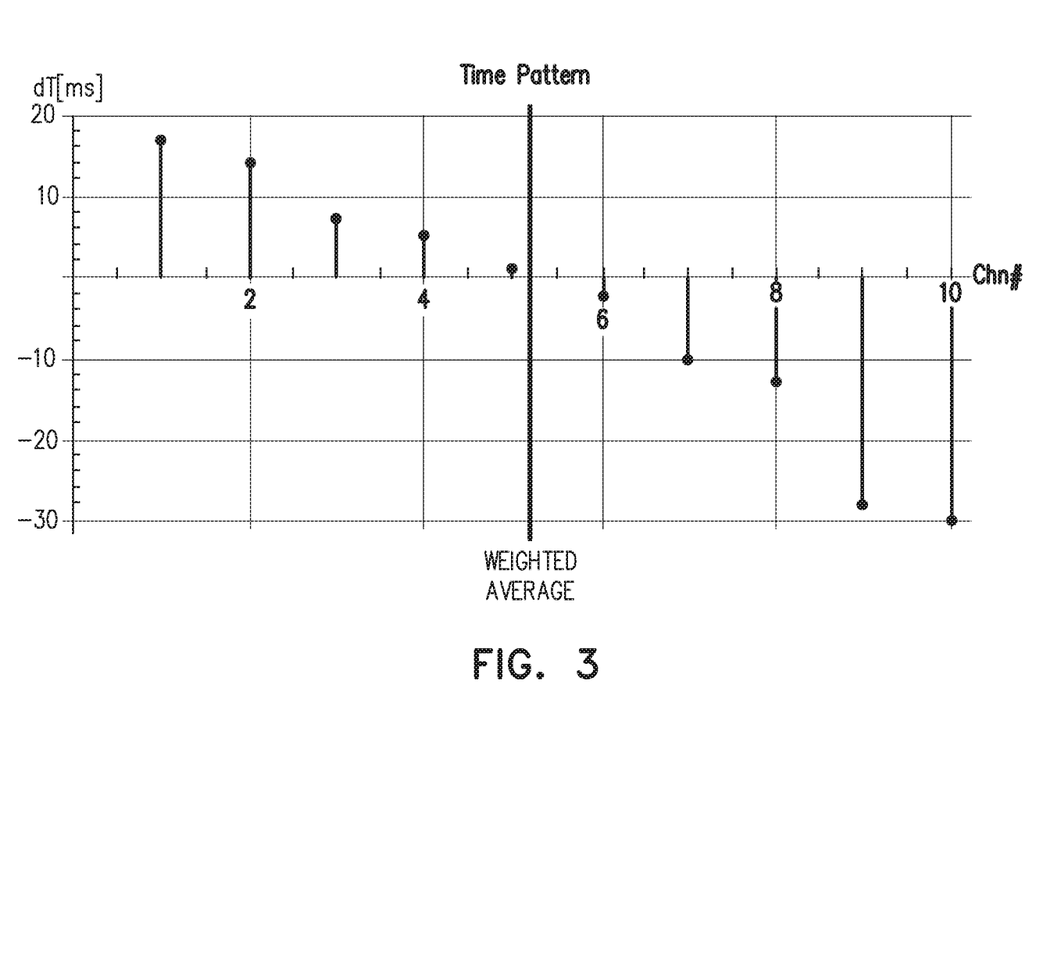
FIG. 3 is a graphical presentation of the time pattern of the signals of FIG. 2, according to an embodiment of the present invention.

An example of unipolar ECG signals with their annotations (solid circles) and their weighted average (black vertical line) is presented in FIG. 2. The processor then calculates the difference between each annotation in the group and the weighted average (dT(k,ti)). The dimensional vector of the differences we call the "time pattern" of this group. A graphical presentation of the time pattern is shown in FIG. 3.

3. Algorithm Description

Processor 10 uses tracker block 22 (FIG. 1) to operate an algorithm working in one of two modes: the Template Tracking (TT) mode and the Template Matching (TM) mode referred to above. The TT mode is typically implemented initially.

Figure 4:
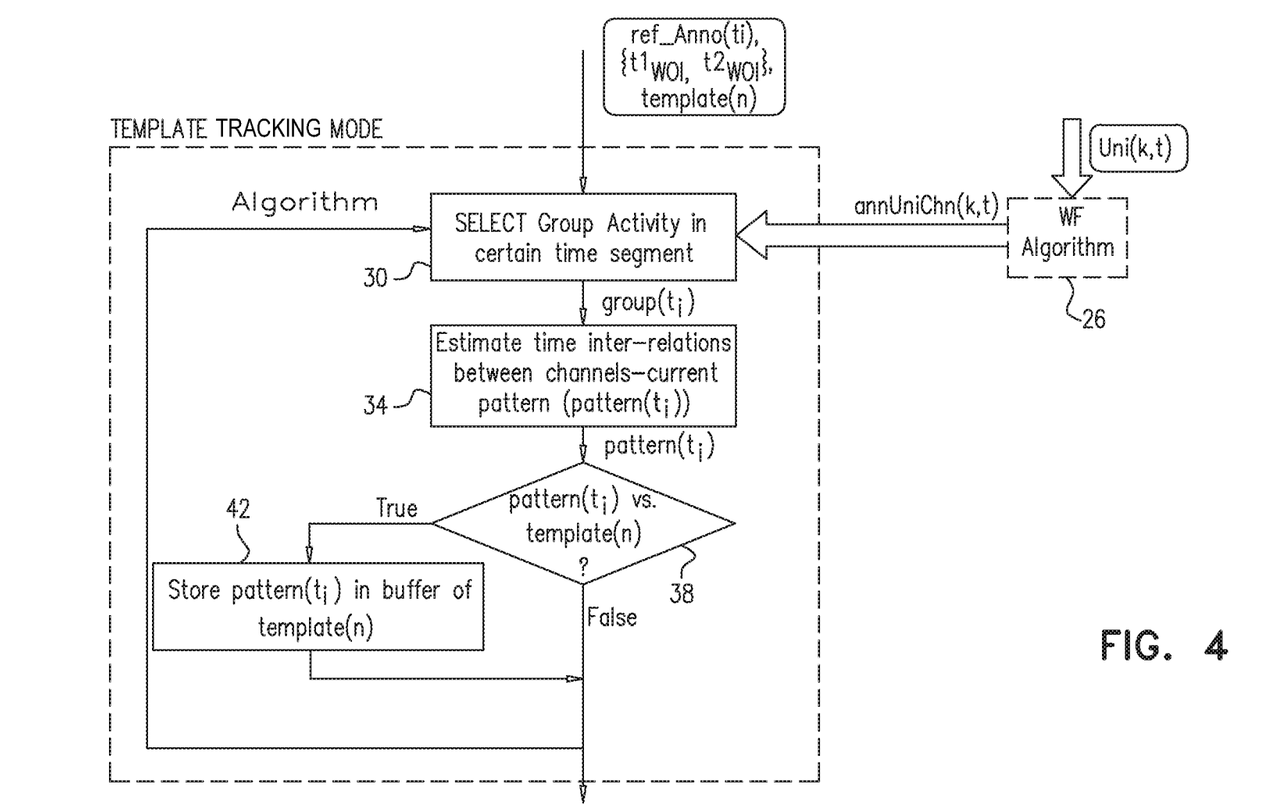
FIG. 4 is a flowchart illustrating steps of a template tracking mode of an algorithm, according to an embodiment of the present invention.

FIG. 4 is a flowchart illustrating steps of the TT mode, according to an embodiment of the present invention. In an initial step 30, the processor initially provides block 22 with a reference annotation (ref_Anno(ti)), a window of interest ({τ1WOI, 2WOI}) and a template of the time pattern (Template(n)). Template(n) is produced in the TM mode, described below, and may be selected by a user of the algorithm. Alternatively, Template(n) may be generated by the user choosing a group of ECG signals from a selected single heartbeat, and using the TM mode to generate the time pattern which then becomes Template(n).

In some embodiments the value of ref_Anno($t_i$) provided by the processor is derived from an external input provided from a user of the algorithm. In alternative embodiments, the processor estimates the value of ref_Anno($t_i$) automatically. The automatic estimation is typically by the processor receiving a stream of channel annotations from wave front annotation block 26, slicing the stream into groups, each group corresponding to a heartbeat, and estimating ref_Anno($t_i$) as one of an average, a weighted average, or a median, of the channel annotations of the groups in the stream.

In the initial step the processor also provides block 22 with values of CS unipolar annotations. The annotations are continually calculated using the wave front algorithm of block 26, and from the stream of the annotations the processor selects a group for a single heartbeat according to the time interval ({ref_Anno(ti)−τ1WOI, ref_Anno(ti)+τ2WOI}).

In a similarity step 34 the processor calculates the time pattern for the current group, as described above in section 2. The calculation gives a k-dimensional vector for the time pattern. The processor then estimates a similarity of the current group to the pre-set template (Template(n)) received in step 30. The similarity is determined by the following formula:

$$s_n(t_i) = \frac{1}{M}\left(\sum_m^M [dT(m, t_i) - dT(m, n)]^2\right)^{0.5} \quad (2)$$

where $s_n(t_i)$ is a value of the similarity between the calculated time pattern {dT(k,ti)} and the vector corresponding to Template(n) {dT(k,n)}, and M is the number of channels in the group of annotations received in step 30. In some embodiments not all channels provide annotations, so that M≤K.

In a decision step 38 the processor checks if $s_n(t_i)$ is less than a pre-set threshold, typically in a range of approximately 0.5—approximately 1.2, although it may be larger or smaller than this range. In this case the decision returns true and the processor recognizes that this group belongs to Template(n), and proceeds to a buffer storage step 42. As is described below with reference to FIG. 6, the processor then presents the result of the identified template on display 18. The flowchart then returns to step 30 to receive a group of annotations for a subsequent heartbeat.

If decision step 38 returns false the flowchart returns to step 30 and the processor processes a new group of values of CS unipolar annotations.

Figure 5:
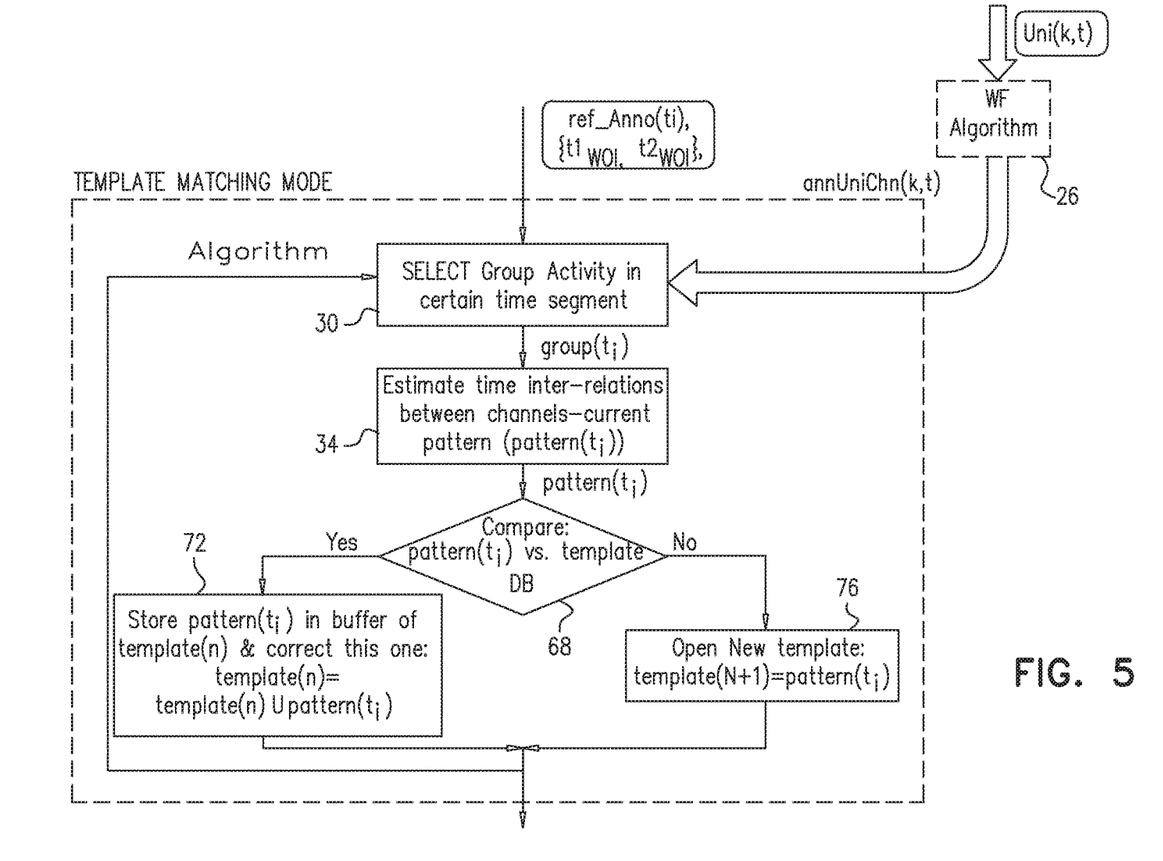
FIG. 5 is a flowchart illustrating steps of a template matching mode of the algorithm, according to an embodiment of the present invention.

FIG. 5 is a flowchart illustrating steps of the TM mode, according to an embodiment of the present invention. Unlike the template tracking mode, the template matching mode doesn't get a template as an input parameter. As shown in FIG. 5, in the TM mode the processor repeats steps 30 and 34 of the TT mode, as described above. In a decision step 68 the TM mode seeks matching between a current time pattern and all templates that have been found before. If step 68 returns false, i.e., if the processor cannot match a template to the current pattern, then in a new template step 76 it opens a new template using the current time pattern, and the new template may be presented on display 18 (described below with reference to FIG. 6).

If the matching is recognized, i.e., if the processor is able to match a template to the current pattern, then in a recalculation step 72 the selected template may be re-calculated to reflect a new member of a cluster of time patterns used to generate the template. The recalculation typically comprises incorporating the values found in step 72 into the calculation of the time pattern by averaging values of dT(k,n) for a number of the groups in the cluster. In some embodiments the recalculation is only performed for the first q members in the cluster, where q may be approximately 10.

Figure 6:
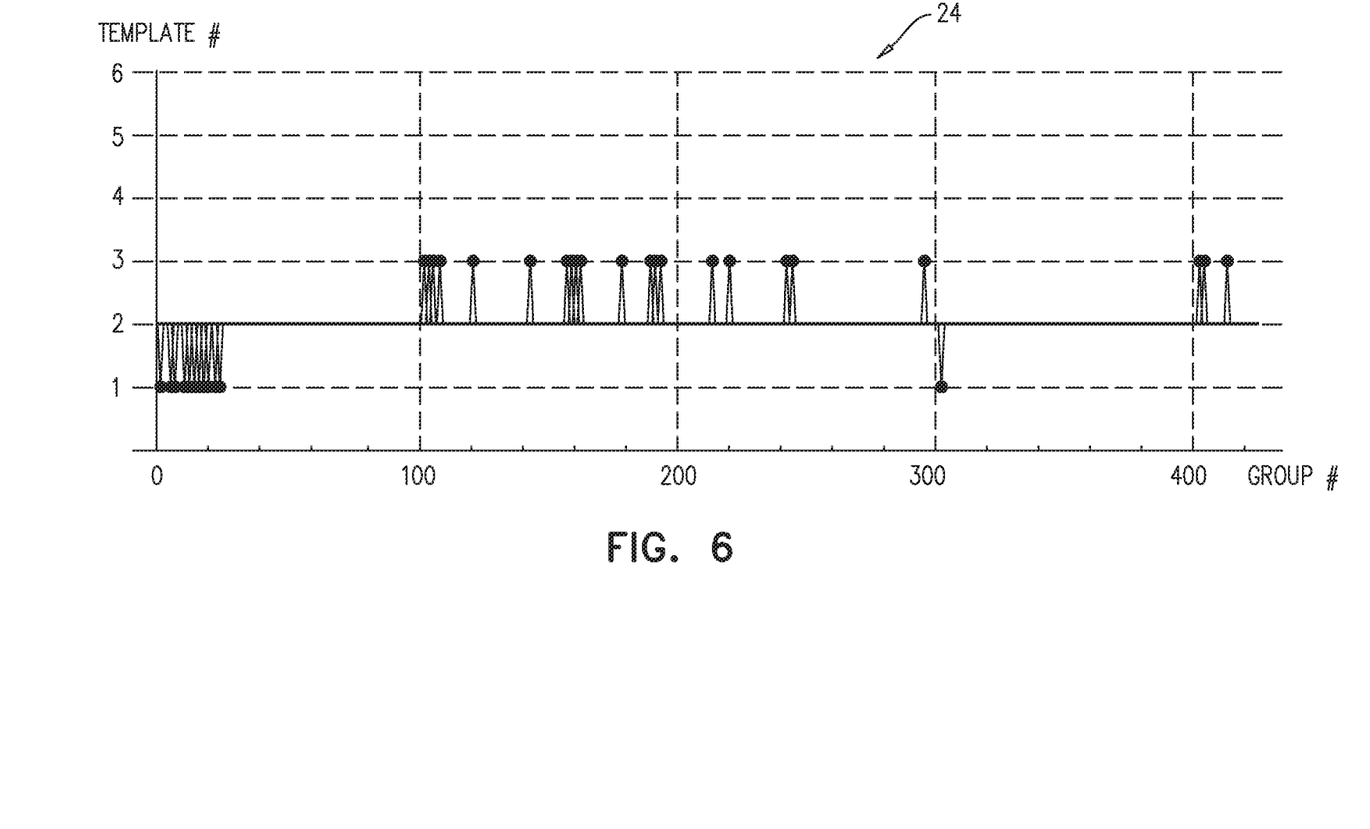
FIG. 6 is a schematic graph of a template number as a function of beat, or group of annotations, number, that is presented on a display, according to an embodiment of the present invention.

FIG. 6 is a schematic graph presented on display 18, according to an embodiment of the present invention. As explained above with reference to step 42, identified templates may be presented on display 18 as a graph 24 (FIG. 1). Graph 24 plots template number vs. group of annotations number, and the group of annotations number corresponds to a timeline of the heartbeats received. As shown in the graph approximately 430 groups have been analyzed, corresponding to the same number of heartbeats. As is also illustrated in the graph, most heartbeats of the timeline are classified as Template 2, but some heartbeats are classified as Template 1 and some are classified as Template 3.

Figure 7:
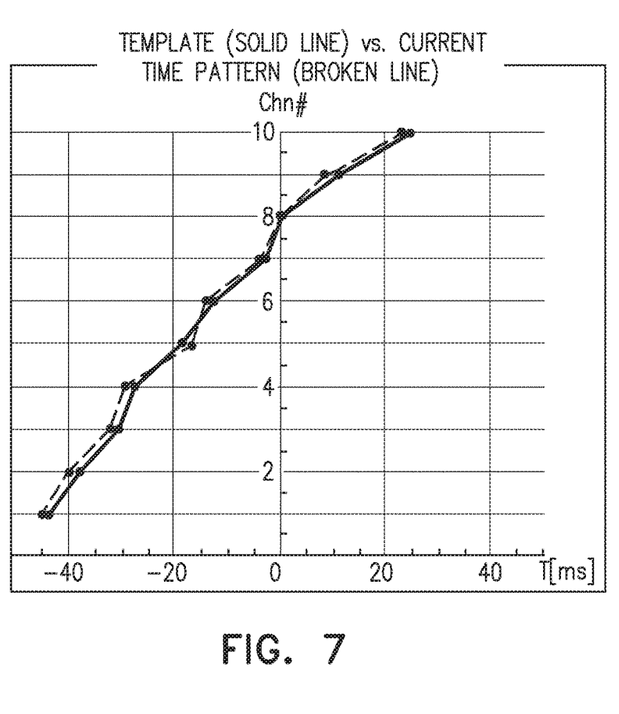
FIG. 7 illustrates a correlation between a template and a group of annotations, according to an embodiment of the present invention.

FIG. 7 illustrates a correlation between a template and a group of annotations, according to an embodiment of the present invention. The figure is a graph of channel number vs. dT for a template based on heartbeat 412, the solid line, and for a group of annotations from heartbeat 463, the broken line, and illustrates the close similarity between the template and the group of annotations being analyzed.

Pairs of graphs such as those illustrated in FIG. 7 typically depict a situation where two heartbeats originate from the same region in the heart.

Figure 8:
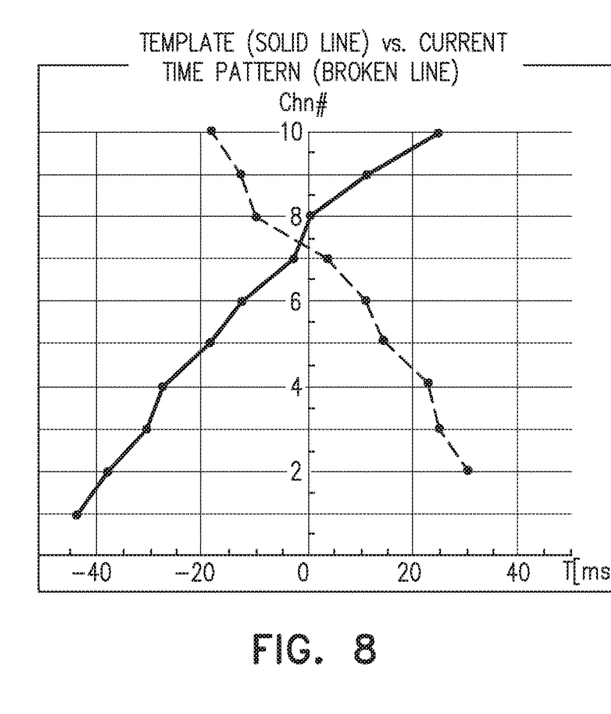
FIG. 8 illustrates an anti-correlation between a template and a group of annotations, according to an embodiment of the present invention.

FIG. 8 illustrates an anti-correlation between a template and a group of annotations, according to an embodiment of the present invention. The figure illustrates how a group of annotations from heartbeat 123, the broken line, does not correlate with the template based on heartbeat 412, the solid line. Rather, since the slopes of the two graphs have opposite signs, there is an anti-correlation between the template and the group of annotations being analyzed.

Pairs of graphs such as those illustrated in FIG. 8 typically occur where two heartbeats originate from two regions in the heart that are separated from each other. For example, such a situation may occur when one region is in the right atrium, and the other region is in the left atrium.

A cardiac electrophysiological map, such as a map of LAT in the heart chambers, is typically produced by acquiring sets of ECG signals, and incorporating results of the signals, i.e., measured LATs, into the map. However, the sets of ECG signals typically include signals having more than one template, and this leads to inaccuracies in the produced map.

Embodiments of the present invention enable the different sets of signals to be separated into subsets, each subset corresponding to a different template. Each subset may be used to construct a respective LAT map of the heart. Thus, returning to FIG. 6, for the three different templates shown in the graph, the acquired signals may be separated into three different subsets, and a map produced for each subset. Typically the different subsets, each for a different template, correspond to different types of arrhythmia.

It will also be appreciated that by analyzing sets of ECG signals as templates, as has been described above, embodiments of the present invention may be used to monitor for a change in arrhythmia, since an arrhythmia change corresponds to a change in template.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
    receiving a first group of electrocardiograph (ECG) signals derived from a single heartbeat and generated at a respective plurality of electrodes on a catheter in a heart of a subject;
    formulating a template relating times of annotations of the first group of the ECG signals, and assigning the template an index;
    receiving a second group of ECG signals derived from a subsequent single heartbeat and generated at the plurality of electrodes;
    calculating times of annotations of the second group of ECG signals;
    formulating a comparison of similarity between the template and a second time pattern relating the times of annotations of the second group, the second time pattern being based on a weighted average of the time of annotations of each ECG signal of the second group; and
    when the comparison indicates that the times of annotations of the second group corresponds to the template within a preset threshold, assigning the index to the second group of ECG signals, and presenting graphically on a display an occurrence of the template relative to a timeline representing the subsequent heartbeat from the heart.

2. The method according to claim 1, and comprising using the first group and the second group to formulate a common map of the heart.

3. The method according to claim 1, and further comprising, when the comparison indicates that the times of annotations of the second group do not correspond to the template, formulating a further template relating the times of annotations of the second group of the ECG signals, and assigning the further template a further index, and presenting graphically on the display a further occurrence of the further template relative to the timeline.

4. The method according to claim 3, and comprising using the first group to formulate a first map of the heart, and the second group to formulate a second map, different from the first map of the heart.

5. The method according to claim 1, and comprising receiving a stream of channel annotations, slicing the stream into segments corresponding to respective heartbeats, estimating a reference annotation as one of an average, a weighted average, or a median, of the channel annotations of the segments in the stream, and applying the reference annotation in formulating the template.

6. The method according to claim 5, wherein the template comprises differences between the times of annotations of the first group with the reference annotation.

7. The method according to claim 1, wherein the catheter is located in a coronary sinus of the heart.

8. The method according to claim 1, wherein the plurality of electrodes are evenly spaced along the catheter.

9. The method according to claim 1, wherein the catheter is linear.

10. The method according to claim 1, wherein the template is assigned to a first type of arrhythmia, the method further comprising receiving a subsequent group of ECG signals, and monitoring if the times of annotations of the subsequent group do not correspond to the template, thus indicating that the subsequent group of ECG signals corresponds to a second type of arrhythmia, different from the first type.

11. The method of claim 1, wherein the template is based on a first time pattern of the first group of ECG signals.

12. The method of claim 1, wherein the second time pattern is based on interrelations between each ECG signal of the second group and the weighted average of the ECG signals of the second group.

13. The method of claim 12, wherein the interrelations is based on a difference between a time annotation of each ECG signal and the weighted time annotation average of the ECG signals of the second group.

14. Apparatus, comprising:
    a catheter, located in a heart of a subject and configured to:
    receive a first group of electrocardiograph (ECG) signals derived from a single heartbeat and generated at a respective plurality of electrodes on the catheter, and
    receive a second group of ECG signals derived from a subsequent single heartbeat and generated at the plurality of electrodes;
    a processor configured to:
    formulate a template relating times of annotations of the first group of the ECG signals, and assign the template an index,
    calculate times of annotations of the second group of ECG signals,
    formulate a comparison of similarity between the template and a second time pattern relating the times of annotations of the second group, the second time pattern being based on a weighted average of the time of annotations of each ECG signal of the second group, and
    when the comparison indicates that the times of annotations of the second group corresponds to the template within a preset threshold, assign the index to the second group of ECG signals; and a display configured to present graphically an occurrence of the template relative to a timeline representing the subsequent heartbeat from the heart.

15. The apparatus according to claim 14, wherein the processor is configured to use the first group and the second group to formulate a common map of the heart.

16. The apparatus according to claim 14, and further comprising, when the comparison indicates that the times of annotations of the second group do not correspond to the template, the processor being configured to formulate a further template relating the times of annotations of the second group of the ECG signals, and to assign the further template a further index, and to present graphically on the display a further occurrence of the further template relative to the timeline.

17. The apparatus according to claim 16, and comprising using the first group to formulate a first map of the heart, and the second group to formulate a second map, different from the first map of the heart.

18. The apparatus according to claim 14, and comprising configuring the processor to receive a stream of channel annotations, slice the stream into segments corresponding to respective heartbeats, estimate a reference annotation as one of an average, a weighted average, or a median, of the channel annotations of the segments in the stream, and apply the reference annotation in formulating the template.

19. The apparatus according to claim 18, wherein the template comprises differences between the times of annotations of the first group with the reference annotation.

20. The apparatus according to claim 14, wherein the catheter is located in a coronary sinus of the heart.

21. The apparatus according to claim 14, wherein the plurality of electrodes are evenly spaced along the catheter.

22. The apparatus according to claim 14, wherein the catheter is linear.

23. The apparatus according to claim 14, wherein the template is assigned to a first type of arrhythmia, and wherein the processor is configured to receive a subsequent group of ECG signals, and monitor if the times of annotations of the subsequent group do not correspond to the template, thus indicating that the subsequent group of ECG signals corresponds to a second type of arrhythmia, different from the first type.

* * * * *